United States Patent [19]

Khanna et al.

[11] 4,439,356

[45] Mar. 27, 1984

[54] UNSYMMETRICAL FLUORESCEIN DERIVATIVES

[75] Inventors: Pyare Khanna, San Jose; Warren Colvin, Redwood City, both of Calif.

[73] Assignee: Syva Company, Palo Alto, Calif.

[21] Appl. No.: 240,031

[22] Filed: Mar. 3, 1981

[51] Int. Cl.$^3$ .................. A61K 39/385; A61K 39/44; C07G 7/00

[52] U.S. Cl. .................. 260/112 R; 260/112 B; 260/112.5 R; 260/112.7; 260/121; 424/85; 424/88; 435/7; 435/188; 525/420; 549/388; 436/172

[58] Field of Search ........ 260/112 R, 112 B, 112.5 R, 260/112.7, 121, 335; 424/8, 12, 85, 88; 435/7, 188; 23/230 B; 525/420; 549/388

[56] References Cited

U.S. PATENT DOCUMENTS

| | | | |
|---|---|---|---|
| 4,220,450 | 9/1980 | Maggio | 435/8 |
| 4,318,846 | 3/1982 | Khanna et al. | 260/121 |
| 4,351,760 | 9/1982 | Khanna et al. | 260/112 R |

*Primary Examiner*—John Kight, III
*Assistant Examiner*—Nathan M. Nutter
*Attorney, Agent, or Firm*—Bertram I. Rowland

[57] ABSTRACT

Unsymmetrically substituted 6-hydroxy-3H-xanthen-3-ones for use as fluorescers or quenchers, particularly conjugated to provide reagents in competitive protein binding assays. Substituents are aliphatic groups bonded to an annular carbon atom through carbon or oxygen.

22 Claims, No Drawings

UNSYMMETRICAL FLUORESCEIN DERIVATIVES

BACKGROUND OF THE INVENTION

1. Field of the Invention

Fluorescent compounds find a wide variety of applications. They find use in fluorescent immunoassays, histochemical staining, displays, inks, and the like. Of particular interest for the subject invention is the use of antigenic conjugates (includes receptor conjugates) with fluorescent compounds to be used in the determination of a variety of ligands, both antigens and receptors. A substantial proportion of the ligands are assayed in physiological fluids, such as serum, where the serum can provide substantial background fluorescence. One way to diminish the background fluorescence resulting from naturally present fluorescers is to provide a fluorescent compound which absorbs at relatively long wavelengths. The compound should desirably have a large Stokes shift, be stable under conditions of the assay, be relatively free of non-specific interference, both from materials in solution and the compound to which the fluorescer is conjugated, and provide high quantum yields. In addition, for certain applications, it is desirable that the fluorescer be coupled with a quencher molecule, that is a molecule which is capable of absorbing the energy of the fluorescer in the excited state, when within a predetermined distance, so that the fluorescer does not fluoresce.

2. Description of the Prior Art

A large number of fluorescein derivatives have been reported in the literature. The following are believed to be the most exemplary in relation to the subject invention and are reported in conjunction with the Chemical Abstracts citation. The numbering is based on the parent molecule 3',6'-dihydroxyspiro [isobenzofuran-1(3H),9'-(9H)xanthen]-3-one.

Asymmetrical fluorescein derivatives without functionalities for attaching to other molecules have been reported in the literature. The following is not intended to be exhaustive of such compounds. The Chemical Abstracts reference is indicated. 2',4'-dichloro-7'-bromo, 2',7'-dichloro-4'-bromo, 2,7'-dibromo-4'-chloro, 2'-bromo-4',7'-dichloro, 2',4'-dibromo-7'-chloro, C.A. 62, 13116C; 2',7'-dibromo-4'-hydroxy, C.A. 61, 7407d; 2',4',7'-tribromo, C.A. 53, 9573h, 65, 4328a; 2',4',7'-trichloro, C.A. 55, 12393f, 63, 6954f; 2',4',5'-triiodo, C.A. 57, 11794b; 2',4',5'-tribromo, C.A. 53, 9573h; 2',4',5'-trichloro, C.A. 55, 12393f, 63, 6954f; 4',5'-dibromo-2'-iodo, C.A. 49, 254e; 4',5'-dinitro-2'-hydroxymercuri, C.A. 51, 313i; 2',5'-dichloro, 2',4'-dichloro, 4'-chloro, 2'-chloro, C.A. 55, 12393f, 63 6954f; 2'-bromo-5'-chloro, C.A. 62, 13116c; 2',5'-dibromo, C.A. 53, 9573g, 71, 8201e; 4'-[(4-sulfamoyl-O-tolyl)azo], 4'-[(p-[2-thiazolylsulfamoyl]phenyl)azo], 4'-[(p-sulfamoylphenyl)azo], 4'-[(6-sulfamoyl-m-tolyl)azo], 4'-[(p-[2-pyridylsulfamoyl]phenyl)azo], C.A. 72, 91456d; 4'-iodo, C.A. 57, 11794c; 4'-chloro, C.A. 63, 6954f, 70, 2018n; 4'-bromo, C.A. 62, 5249b, 71, 8201c; 2'-pentenyl, 2'-allyl, C.A. 31, 1388; 2'-benzyl, C.A. 74, 45540v; 2'-bromo, C.A. 53, 9573h, 62, 5249c, 71, 8201c.

Symmetrical fluorescein derivatives, having alkyl or oxy substituents may be found in co-pending applications Ser. No. 73,158, filed Sept. 7, 1979 and 73,163, filed Sept. 7, 1979, now U.S. Pat. Nos. 4,318,846 and 4,351,760, respectively.

DESCRIPTION OF THE SPECIFIC EMBODIMENTS

Unsymmetrical fluorescein derivatives are provided having high Stokes shifts and high quantum yields. The compounds can be used where interference is observed due to the presence of endogenous fluorescers having absorption at longer wavelengths, such as found in serum. The compounds can also be used as conjugates to make other compounds or substrates fluorescent, as labels in histochemistry, cytology, and diagnostic assays. Depending upon the substituents employed on the fluorescein, the compound can be fluorescent or be non-fluorescent and capable of acting as a quencher.

The subject invention concerns fluorescent compounds, which are analogs of fluorescein, being particularly 1,8-unsubstituted-9-substituted-6-hydroxy-3H-xanthen-3-ones, having one aliphatic substituent at any of the remaining positions, where the aliphatic substituent is separated from the annular carbon atom by from 0 to 1 oxygen atom. Normally present will be a functionality, particularly a non-oxo-carbonyl functionality, for conjugation to a member of an immunological pair, referred to as a ligand and receptor. For convenience, the member of the immunological pair will be abbreviated as "mip". The conjugates to the mip find particular use as reagents in assays for determining a mip.

The fluorescent precursors will have at least about 14 carbon atoms, usually about 20 carbon atoms, and usually not more than about 40 carbon atoms, usually having from about 21 to 35 carbon atoms. Preferably there is at least one, usually two chlorine atoms at other than the 1,8-positions and there may be as many as 7 chlorine atoms. In addition to chlorine, the only other heteroatoms are fluorine, bromine, and iodine, chalcogen, particularly oxygen and sulfur, and nitrogen, there being at least 4 heteroatoms and usually not more than 20 heteroatoms, more usually not more than about 16 heteroatoms and preferably not more than about 12 heteroatoms. Of the heteroatoms other than chlorine, there will be at least 3 oxygen atoms, more usually at least 5 oxygen atoms, and other than the oxygen atoms, which are part of the xanthene chromophore, are oxygen atoms as non-oxo-carbonyl or oxy, particularly acid, ester or ether (normally bonded solely to carbon and hydrogen); sulfur is normally present as sulfonyl, thioether or mercapto; while nitrogen is normally present as amino or amido (bonded solely to carbon and hydrogen).

The fluorescent compounds are further characterized by having absorption maxima in 0.5 M phosphate buffer pH 8 of at least about 490 nm, usually at least about 500 nm, an extinction coefficient in the same medium of at least about 65,000 $M^{-1}cm^{-1}$, more usually at least 70,000 and a Stokes shift in the same medium of at least about 10 nm, more usually at least about 12 nm.

The 9-substituted-xanthenes of this invention will for the most part have the following formula:

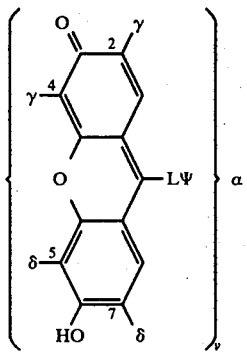

wherein:
one of the γ's will be of the formula —(O)$_\epsilon\rho$ and the other is δ;

wherein:
O stands for its normal meaning of oxygen;
$\epsilon$ is zero or one;
ρ is an aliphatic group, normally aliphatic hydrocarbon or substituted aliphatic hydrocarbon, usually monosubstituted, saturated or unsaturated, branched or straight chain, particularly alkyl or carboxyalkyl of from 1 to 12, usually 1 to 6, more usually 1 to 4 carbon atoms, and having from 0–1 carboxyl groups;
δ is hydrogen, or halogen of atomic number 17 to 80, the δ's may be the same or different;
L is a bond or divalent radical, usually an organic radical, of at least one carbon atom and not more than 20, usually not more than 16, more usually not more than 10 carbon atoms, normally having an aliphatic or aromatic hydrocarbon chain or combination thereof, wherein the aliphatic chain is usually of from about 2 to 6 carbon atoms, and the aromatic chain of from about 6 to 12, usually 6 to 10 carbon atoms; L normally has from 0 to 4, when aromatic, usually 1 to 4, more usually 2 to 4 substituents, wherein the substituents may be halo, particularly chloro, non-oxo-carbonyl, thio, including inert sulfur acids, esters and amides, amino, particularly tert-amino or amido, and oxy; wherein the substituents are normally of from 0 to 4 carbon atoms, there being at least two carbon atoms between heteroatoms bonded to saturated carbon atoms; when L is a benzene ring, 4 will be at other than the ortho position to the xanthenone.

α may be taken together with Ψ to define an active group capable of forming a stable covalent bond with carbon, nitrogen or oxygen or is an organic compound, usually a member of a specific binding pair, either a ligand or receptor; the covalent bond formed between Ψ and α normally involves an amido, methylene, sec-amino, ether, thio, or azo link, with the proviso that when ρ has a carboxyl substituent, α may be taken together with Ψ to define H, oxy, or halo of atomic number 9 to 80;

Ψ is a group terminating in a heteroatom containing functionality when not taken together with α, wherein the terminal heteroatom containing functionality may be bonded directly to a carbon atom of L or through an oligomer of from 1 to 4 units, each unit of 1 to 4, usually 2 to 4 carbon atoms, which units are amino acids of from 2 to 4 carbon atoms, alkyleneamino or alkyleneoxy groups; the terminal functionality is normally oxo, including oxo-carbonyl and non-oxo-carbonyl; amino; oxy; thio; or active halogen; particularly non-oxo-carbonyl; and v is 1 when Ψ is taken together with α to form an active group, and is otherwise on the average of at least 1 and not more than the molecular weight of α divided by 500, usually divided by 5,000.

When ε is 0, that is, one of the γ's is an aliphatic group, one of the δ's may be an aliphatic group coming within the definition of ρ, where the two aliphatic groups are asymmetrically positioned. The numerical value of the positions to which the aliphatic groups are bonded will add up to other than nine. Therefore, the dialiphatic substituted xanthenones would be 2,4-, 2,5- and 4,7-substituted.

Desirably, there are from 0 to 6, more usually from 1 to 6 chloro substituents on the fluorescent group (in the brackets), bonded at other than the 1,8-positions of the xanthenone. Also, while there may be only one oxy substituent at any of the positions, 2,4,5, and 7, there may be up to two aliphatic substituents where ε is 0, and the sum of the positions of the alkyl substituents adds up to other than 9.

For the most part, the compounds of this invention will have a 9-phenyl substituent and will be of the following formula:

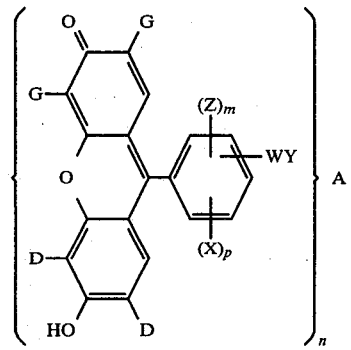

wherein:
one of the Gs is of the formula —(O)$_e$R:
wherein:
e is 0 or 1;
R is an aliphatic group of from 1 to 6, usually 1 to 4, more usually 1 to 3 carbon atoms, which may be substituted or unsubstituted, aliphatically saturated or unsaturated, usually saturated, but particularly alkyl or carboxyalkyl of from 1 to 4, usually 1 to 3 carbon atoms;
when other than of the formula —(O)$_e$R, G will come within the definition of D;
Z is carboxy or sulphonoxy;
D is hydrogen or halogen of atomic number 17 to 80, usually 17 to 35;
W is a bond or divalent organic radical having from 0 to 16, either 0 or from 1 to 10, more usually 1 to 8, preferably 1 to 6 carbon atoms and from 0 to 8, usually 2 to 8, more usually 2 to 6 heteroatoms, which are chalcogen, (oxygen and sulfur) or nitrogen; wherein chalcogen is present bonded solely to carbon (oxy or oxo) and nitrogen is present bonded solely to carbon and hydrogen (amino and amido); carbon is normally aromatic or aliphatic, particularly free of aliphatic unsaturation, having from 0 to 2 sites of ethylenic unsaturation, preferably saturated; W is conveniently a monomer or oligomer of units of from 1 to 4 carbon atoms e.g. alkylene, amino acid, oxyalkylene, aminoalkylene, etc;

Y may be taken together with A to form an active functionality capable of forming a covalent bond with a heterofunctionality, such as amino, hydroxy, or mercapto; that is, with those functionalities present on A, when A is other than taken together with Y. Y and A taken together are functionalities such as oxo, either oxo- or non-oxo-carbonyl, oxy, thio, amino, active halo, active olefin, inorganic acyl group, e.g. sulfonyl, etc., or when not taken together with A, Y acts as a linking functionality, being either methylene or heteroatom containing, e.g., non-oxo-carbonyl, thiourea, sulfonyl, oxy, imino, etc.; when W and Y are taken together to define carboxy, usually non-oxo-carbonyl WY will be at other than the ortho position;

A, when not taken together with Y, is a member of a specific binding pair, which is a ligand or receptor, wherein the ligand may be haptenic or antigenic, normally being of from about 125 molecular weight to a indefinite upper limit. Although for the most part, most ligands will be under 10 million molecular weight, more usually under 2 million molecular weight, with varying ranges depending upon the nature of the ligand or receptor, of particular interest are poly(amino acid) ligands or receptors of from about 1,000 to 500,000 molecular weight;

X is halo, usually of atomic number 9 to 80, more usually 9 to 35, particularly chloro;

m is 0 to 3, more usually 1 to 2;

p is 0 to 3, with the sum of m and p being not greater than 4; and, n will be 1 when Y and A are taken together and will otherwise be on the average 1 to the molecular weight of A divided by 500, more usually divided by 1,000, and more frequently divided by 2,000, wherein with specific binding pair members over 600,000 molecular weight, it will normally be not greater than A divided by 5,000. Furthermore, either the conjugate or the fluorescer precursor may be bonded to a support of at least about 10,000 molecular weight and up to an indefinite molecular weight.

A preferred group of compounds have the following formula:

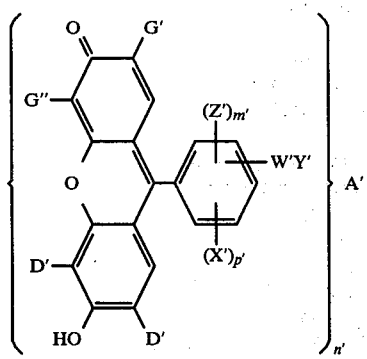

wherein:
one of G' or G", preferably G' is —(O)$_{e'}$R';
wherein:

e' is 0 or 1, preferably 1 and

R' is alkyl of from 1 to 6, more usually of from 1 to 3 carbon atoms;

the other of G' and G" will come within the definition of D';

X' and Z' come within the definitions of X and Z, respectively;

D' is hydrogen or halogen of atomic number 17 to 80, usually 17 to 35, and preferably chloro;

Y' may be taken together with A' to define a non-oxo-carbonyl group or when not taken together with A' is a non-oxo-carbonyl linking group to A', usually forming an amide link; when taken together with A' to define carboxy, —W'Y' will be at other than the ortho position;

W' is a bond or linking group, usually aliphatic, of from 1 to 12, usually 1 to 8 atoms other than hydrogen, which are carbon, nitrogen, oxygen or sulfur, preferably carbon, nitrogen, and oxygen, there being from 0 to 8 carbon atoms and 0 to 8 heteroatoms, preferably 0 to 4 heteroatoms, with then number of carbon atoms and hetero atoms being at least 1, wherein nitrogen will be bonded solely to hydrogen and carbon and will be either amino or amido, oxygen and sulfur will be bonded solely to carbon as oxy(thio) or oxo(thiono) and carbon is normally aliphatic, usually free of aliphatic unsaturation, generally having from 0 to 1 site of ethylenic unsaturation; W' may be alkylene, alkenylene, oxyalkylene, or oxoalkylene of from 1 to 8, usually 1 to 4 carbon atoms, imino (NH), N-formyl amino acid or N-formyl poly(amino acid) e.g. glycine or polyglycine, there being from 1 to 4, usually 1 to 2, amino acids of from 2 to 4 carbon atoms, with the terminal carboxy being Y';

n' is 1 when Y' and A' are taken together and otherwise is on the average at least 1 to the molecular weight of A' divided by 500, usually divided by 1,000, and more usually divided by 2,000, and when A' is over 500,000 molecular weight, more usually divided by 5,000;

m' is 0 to 2, usually 0 to 1;

p' is 0 to 3, more usually 0 to 2, the sum of m' and p' being not greater than 4;

there generally being not more than three carboxyl groups, more usually not more than about two carboxyl groups in total, and there being from about 0 to 6 chloro groups, more usually from about 0 to 5 chloro groups, and preferably from about 2 to 5 chloro groups; and A' when not taken together with Y' is a member of a specific binding pair, a ligand or receptor, wherein the ligand may be haptenic or antigenic, where haptenic ligands will include compounds of interest such as drugs, hormones, pollutants, processing compounds, agricultural chemicals, metabolites, and the like; antigens will primarily be proteins, polysaccharides, or nucleic acids, individually or in combination with each other, or other materials involving combinations of compounds, such as cells, viruses, phage, or the like. The haptens will normally be from about 125 to 2,000 daltons, more usually to 1,000 daltons, while the antigens will normally be from about 2,000, more usually 5,000 daltons up to an indefinite molecular weight, usually not exceeding 10 million daltons, more usually not exceeding 2 millions daltons.

Preferably, three of the 2,4,5, and 7 positions will be unsubstituted or chloro substituted.

In some instances, it may be desirable to have the fluorescent compound or the conjugate of the fluorescent compound with the ligand or receptor, bonded to a support, where the linkage may be derived from either the fluorescent compound or the ligand or receptor compound. In this situation, the linking group may be any conventional functionality which is present on the fluorescent compound or the ligand or receptor, or a functionality which may be introduced onto any of these compounds.

The supports will include macromolecular supports of at least about 10,000 molecular weight, which may be naturally occurring or synthetic, having a plurality of functionalities for linking e.g. carboxy, hydroxy, or amino, usually being a polymer, such as a polysaccharide or an addition polymer.

Quite obviously, the compounds of the subject invention can be modified so as not to be within the above formulas, without significantly affecting the properties of the compounds. For example, one or more of the acidic anionic groups can be esterified or amidified or alkyl groups can be substituted on the phenyl as well as other groups, such as cyano, nitro or the like. However, these changes will in most cases require additional synthetic steps which are not warrented by the degree of enhancement, if any, in the spectroscopic or chemical properties of the resulting product.

Turning now to a consideration of the individual components of the subject compositions, the fluorescein derivatives will be considered first. The following is a list of illustrative fluorescein derivatives coming within the scope of the subject invention.

TABLE I 2-methyl-4,5-dichloro-9-(2',4',5'-tricarboxyphenyl) -6-hydroxy-3H-xanthen-3-one
2-ethyl-4,5-dichloro-9-(2',4',5'-tricarboxy-3',6'-dichlorophenyl)-6-hydroxy-3H-xanthen-3-one
2-hexyl-9-(2',4',5'-tricarboxyphenyl)-6-hydroxy-3H-xanthen-3-one
2-methyl-4,5-dichloro-9-(2'-carboxy-4'-isothiocyanato-3',5'-dichlorophenyl)-6-hydroxy-3H-xanthen-3-one
2-methyl-9-(2'-carboxy-4'-isocyanato-3',5',6'-trichlorophenyl)-6-hydroxy-3H-xanthen-3-one
2-methyl-9-(4'-carboxamidoacetamidoglycylglycine-5'-carboxylphenyl)-6-hydroxy-3H-xanthen-3-one
2-propoxy-9-(4',5',-dicarboxy-2',3',6'-trichlorophenyl)-6-hydroxy-3H-xanthen-3-one
2-ethoxy-4,5-dichloro-9-(3',4'-dicarboxyphenyl)-6-hydroxy-3H-xanthen-3-one
2-ethyl-9-(2'-carboxy-4'-amino-3',5'-dichlorphenyl)-6-hydroxy-3H-xanthen-3-one
4-ethyl-9-(2'-carboxy-4'-mercaptophenyl)-6-hydroxy-3H-xanthen-3-one
4-ethoxy-9-(2'-carboxy-4'-carboxymethylphenyl)-6-hydroxy-3H-xanthen-3-one
2-ethoxy-9-(2'-carboxy-4'-(4''-carboxybutyl)-phenyl)-6-hydroxy-3H-xanthen-3-one
2-methoxy-4,5-dichloro-9-(2',4'-dicarboxy-5'-(carboxyamidomethylene)phenyl)-6-hydroxy-3H-xanthen-3-one
2 methyl-4,5-dichloro-9(3'-carboxypropyl)-6-hydroxy-3H-xanthen-3-one.

As indicated previously, the fluorescein derivatives of the subject invention will be conjugated with ligands and/or supports. The following is a description of the applicable ligands.

Analyte

The ligand analytes of this invention are characterized by being monoepitopic or polyepitopic. The polyepitopic ligand analytes will normally be poly(amino acids) i.e. polypeptides and proteins, polysaccharides, nucleic acids, and combinations thereof. Such combinations of assemblages include bacteria, viruses, chromosomes, genes, mitochondria, nuclei, cell membranes, and the like.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The wide variety of proteins may be considered as to the family of proteins having similar structural features, proteins having particular biological functions, proteins related to specific microorganisms, particularly disease causing microorganisms, etc.

The following are classes of proteins related by structure:
protamines
histones
albumins
globulins
scleroproteins
phosphoproteins
mucoproteins
chromoproteins
lipoproteins
nucleoproteins
glycoproteins
proteoglycans
unclassified proteins, e.g. somatotropin, prolactin, insulin, pepsin A number of proteins found in the human plasma are important clinically and include:
Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S -Postalbumin
Tryptophan-poor
$\alpha_1$-glycoprotein
$\alpha_1$X-Glycoprotein
Thyroxin-binding globulin
Inter-$\alpha$-trypsin-inhibitor
Gc-globulin
(Gc 1-1)
(Gc 2-1)
(Gc 2-2)
Haptoglobin
(HP 1-1)
(HP 2-1)
(Hp 2-2)
Ceruloplasmin
Cholinesterase α$_2$-Lipoprotein(s)
Myoglobin
C-Reactive Protein
α$_2$-Macroglobulin
α$_2$-HS-glycoprotein
Zn-α$_2$-glycoprotein
α$_2$-Neuramino-glycoprotein
Erythropoietin
β-lipoprotein
Transferrin
Hemopexin
Fibrinogen
Plasminogen
β$_2$-glycoprotein I
β$_2$-glycoprotein II
Immunoglobulin G
   (IgG) of γG-globulin
Mol. formula:
   γ$_2$κ$_2$ or γ$_2$λ$_2$
Immunoglobulin A (IgA)
   or γA-globulin
Mol. formula:
   (α$_2$κ$_2$)$^n$ or (α$_2$λ$_2$)$^n$
Immunoglobulin M
   (IgM) or γM-globulin
Mol. formula:
   (μ$_2$κ$_2$)$^5$ or (μ$_2$λ$_2$)$^5$
Immunoglobulin D(IgD)
   or γD-Globulin (γD)
Mol. formula:
   δ$_2$κ$_2$) or δ$_2$λ$_2$)
Immunoglobulin E (IgE)
   or γE-Globulin (γE)
Mol. formula:
   (ε$_2$κ$_2$) or (ε$_2$λ$_2$)
Free κ and λ light chains
Complement factors:
C'1
   C'1q
   C'1r
   C'1s
C'2
C'3
   β$_1$A
   α$_2$D
C'4
C'5
C'6
C'7
C'8
C'9
Important blood clotting factors include:

| BLOOD CLOTTING FACTORS | |
| --- | --- |
| International designation | Name |
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:
Peptide and Protein Hormones
   Parathyroid hormone (parathromone)
   Thyrocalcitonin
   Insulin
   Glucagon
   Relaxin
   Erythropoietin
   Melanotropin (melanocyte-stimulating hormone; intermedin)
   Somatotropin (growth hormone)
   Corticotropin (adrenocorticotropic hormone)
   Thyrotropin
   Follicle-stimulating hormone
   Luteinizing hormone (interstitial cell-stimulating hormone)
   Luteomammotropic hormone (luteotropin, prolactin)
   Gonadotropin (chorionic gonadotropin)
Tissue Hormones
   Secretin
   Gastrin
   Angiotensin I and II
   Bradykinin
   Human placental lactogen
Peptide Hormones from the Neurohypophysis
   Oxytocin
   Vasopressin
   Releasing factors (RF) CRF, LRF, TRF, Somatotropin-RF, GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
| --- | --- |
| Streptococcus pyogenes | Polysaccharide |
| Diplococcus pneumoniae | Polysaccharide |
| Neisseria meningitidis | Polysaccharide |
| Neisseria gonorrheae | Polysaccharide |
| Corynebacterium diphtheriae | Polysaccharide |
| Actinobacillus mallei; Actinobacillus whitemori | Crude extract |
| Francisella tularensis | Lipopolysaccharide Polysaccharide |
| Pasteurella pestis | |
| Pasteurella pestis | Polysaccharide |
| Pasteurella multocida | Capsular antigen |
| Brucella abortus | Crude extract |
| Haemophilus influenzae | Polysaccharide |
| Haemophilus pertussis | Crude |
| Treponema reiteri | Polysaccharide |
| Veillonella | Lipopolysaccharide |
| Erysipelothrix | Polysaccharide |
| Listeria monocytogenes | Polysaccharide |
| Chromobacterium | Lipopolysaccharide |
| Mycobacterium tuberculosis | Saline extract of 90% phenol extracted mycobacteria and polysaccharide fraction of |

-continued

| Species of Microorganisms | Hemosensitin Found in |
|---|---|
|  | cells and turberculin |
| Klebsiella aerogenes | Polysaccharide |
| Klebsiella cloacae | Polysaccharide |
| Salmonella typhosa | Lipopolysaccharide, Polysaccharide |
| Salmonella typhi-murium; Salmonella derby Salmonella pullorum | Polysaccharide |
| Shigella dysenteriae Shigella flexneri | Polysaccharide |
| Shigella sonnei | Crude, Polysaccharide |
| Rickettsiae | Crude extract |
| Candida albicans | Polysaccharide |
| Entamoeba histolytica | Crude extract |

The microorganisms which are assayed may be intact, lysed, ground or otherwise fragmented, and the resulting composition or portion, e.g. by extraction, assayed. Microorganisms of interest include:

Corynebacteria
  Corynebacterium diptheriae
Pneumococci
  Diplococcus pneumoniae
Streptococci
  Streptococcus pyogenes
  Streptococcus salivarus
Staphylococci
  Staphylococcus aureus
  Staphylococcus albus
Neisseriae
  Neisseria meningitidis
  Neisseria gonorrheae
Enterobacteriaciae
   The coliform bacteria
  Escherichia coli
  Aerobacter aerogenes
  Klebsiella pneumoniae
   The Salmonellae
  Salmonella typhosa
  Salmonella choleraesuis
  Salmonella typhimurium
   The Shigellae
  Shigella dysenteriae
  Shigella schmitzii
  Shigella arabinotarda
  Shigella flexneri
  Shigella boydii
  Shigella Sonnei
Other enteric bacilli
   Proteus species
  Proteus vulgaris
  Proteus mirabilis
  Proteus morgani
  Pseudomonas aeruginosa
  Alcaligenes faecalis
  Vibrio cholerae
Hemophilus-Bordetella group
  Hemophilus influenzae, H. ducreyi, H. hemophilus, H. aegypticus, H. parainfluenzae,
  Bordetella pertussis
Pasteurellae
  Pasteurella pestis
  Pasteurella tulareusis
Brucellae
  Brucella melitensis
  Brucella abortus
  Brucella suis
Aerobic Spore-forming Bacilli
  Bacillus anthracis
  Bacillus subtilis
  Bacillus megaterium
  Bacillus cereus
Anaerobic Spore-forming Bacilli
  Clostridium botulinum
  Clostridium tetani
  Clostridium perfringens
  Clostridium novyi
  Clostridium septicum
  Clostridium histolyticum
  Clostridium tertium
  Clostridium bifermentans
  Clostridium sporogenes
Mycobacteria
  Mycobacterium tuberculosis hominis
  Mycobacterium bovis
  Mycobacterium avium
  Mycobacterium leprae
  Mycobacterium paratuberculosis
Actinomycetes (fungus-like bacteria)
  Actinomyces israelii
  Actinomyces bovis
  Actinomyces naeslundii
  Nocardia asteroides
  Nocardia brasiliensis
The Spirochetes
  Treponema pallidum
  Treponema pertenue
  Spirillum minus
  Streptobacillus moniliformis
  Treponema carateum
  Borrelia recurrentis
  Leptospira icterohemorrhagiae
  Leptospira canicola
Mycoplasmas
  Mycoplasma pneumoniae
Other pathogens
  Listeria monocytogenes
  Erysipelothrix rhusiopathiae
  Streptobacillus moniliformis
  Donvania granulomatis
  Bartonella bacilliformis
Rickettsiae (bacteria-like parasites)
  Rickettsia prowazekii
  Rickettsia mooseri
  Rickettsia rickettsii
  Rickettsia conori
  Rickettsia australis
  Rickettsia sibiricus
  Rickettsia akari
  Rickettsia tsutsugamushi
  Rickettsia burnetii
  Rickettsia quintana
Chlamydia (unclassifiable parasites bacterial/viral)
  Chlamydia agents (naming uncertain)
Fungi
  Cryptococcus neoformans
  Blastomyces dermatidis
  Histoplasma capsulatum
  Coccidioides immitis
  Paracoccidioides brasiliensis
  Candida albicans

*Aspergillus fumigatus*
*Mucor corymbifer (Absidia corymbifera)*
  Phycomycetes
*Rhizopus oryzae*
*Rhizopus arrhizus*
*Rhizopus nigricans*
*Sporotrichum schenkii*
*Fonsecaea pedrosoi*
*Fonsecaea compacta*
*Fonsecaea dermatidis*
*Cladosporium carrionii*
*Phialophora verrucosa*
*Aspergillus nidulans*
Madurella mycetomi
Madurella grisea
*Allescheria boydii*
Phialosphora jeanselmei
*Microsporum gypseum*
*Trichophyton mentagrophytes*
*Keratinomyces ajelloi*
*Microsporum canis*
*Trichophyton rubrum*
*Microsporum andouini*
Viruses
Adenoviruses
Herpes Viruses
  Herpes simplex
  Varicella (Chicken pox)
  Herpes Zoster (Shingles)
  Virus B
  Cytomegalovirus
Pox Viruses
  Variola (smallpox)
  Vaccinia
  *Poxvirus bovis*
  Paravaccinia
  *Molluscum contagiosum*
Picornaviruses
  Poliovirus
  Coxsackievirus
  Echoviruses
  Rhinoviruses
Myxoviruses
  Influenza (A, B, and C)
  Parainfluenza (1-4)
  Mumps Virus
  Newcastle Disease Virus
  Measles Virus
  Rinderpest Virus
  Canine Distempeer Virus
  Respiratory Syncytial Virus
  Rubella Virus
Arboviruses
  Eastern Equine Eucephalitis Virus
  Western Equine Eucephalitis Virus
  Sindbis Virus
  Chikugunya Virus
  Semliki Forest Virus
  Mayora Virus
  St. Louis Encephalitis Virus
  California Encephalitis Virus
  Colorado Tick Fever Virus
  Yellow Fever Virus
  Dengue Virus
Reoviruses
  Reovirus Types 1-3
Hepatitis
  Hepatitis A Virus
  Hepatitis B Virus
Tumor Viruses
  Rauscher Leukemia Virus
  Gross Virus
  Maloney Leukemia Virus The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazoyl alkaloids; quinazoline alkaloids, isoquinoline alkaloids; quinoline alkaloids; which includes quinine and quinidine; diterpene alkaloids; their derivatives and metabolites.

The next group of drugs includes steroids, which includes the estrogens, gestogens, androgens, andrenocortical steroids, bile acids, cardiotonic glycosides and aglycones, which includes digoxin and digoxigenin, saponins and sapogenins, their derivatives and metabolites. Also included are the steriod mimetic substances, such as diethylstilbestrol.

The next group of drugs is lactams having from 5 to 6 annular members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, their metabolites.

The next group of drugs is aminoalkylbenzenes, with alkyl of from 2 to 3 carbon atoms, which includes ephedrine, L-dopa, epinephrine, narceine, papaverine, their metabolites and derivatives.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, their metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

The next group of compounds is amino acids and small peptides which include polyiodothyronines e.g. thyroxine, and triiodothyronine, oxytocin, ACTH, angiotensin, met- and leu-enkephalin their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^6$, more usually from 10,000 to $10^6$. For immunoglobulins, IgA, IgG, IgE and IgM, the molecular weights will generally vary from about 160,000 to about $10^6$. Enzymes will normally range from about 10,000 to 6,000,000 in molecular weight. Natural receptors vary widely, generally being at least about 15,000 molecular weight and may be $10^6$ or higher molecular weight, including such materials as avidin, thyroxine binding globulin, thyroxine binding prealbumin, transcortin, etc.

In many applications of the subject fluorescein derivatives, it will be desirable to have the ligand bonded to a support, either directly, through the intermediacy of a ligand, or directly to the support, while bound to a ligand.

A wide variety of supports may be employed. The particles or supports can be derived from naturally occurring materials, naturally occurring materials which are synthetically modified and synthetic materials. Of particular interest are polysaccharides, particularly crosslinked polysaccharides, such as agarose, which is available as Sepharose, dextran, available as Sephadex and Sephacyl, cellulose, starch, and the like. Other materials include polyacrylamides, polystyrene, polyvinyl alcohol, copolymers of hydroxyethyl methacrylate and methyl methacrylate, silicones, glasses, available as Bioglas, nucleic acids, poly(amino acids), cells or the like. In addition to solid particles, liquid particles may also be employed having a lipophilic or amphiphilic membrane, which serves to contain an internal fluid and define a space. Such particles include vesicles, cells and liposomes.

The particles may be porous or nonporous, swellable or nonswellable by aqueous or organic media, normally having a variety of functionalities, such as hydroxyl, amino or carboxy, either bonded directly to the backbone or by means of a spacer arm, crosslinked or non-crosslinked, smooth or rough surface, or the like.

The porous particles may have a wide variety of cut off sizes, generally varying from about 10,000 to many million molecular weight, usually not exceeding 20 million molecular weight.

As already indicated, a wide variety of linking chains may be employed between the fluorescein compound and the ligand and/or support. The choice of linking group will vary widely, depending upon the available functionalities or functionalities which may be readily introduced, the desired length of the linking arm, the desirability of having the linking arm provide for a particular environment, chemical property or physical property, e.g. positively or negatively charged, solubility enhancement, dipole effects, or the like.

The following table indicates a variety of linking groups which may be employed for linking the fluorescein compound to the ligand:

TABLE II

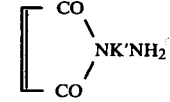

wherein:

K is alkylene of from 1 to 8, usually 1 to 6 carbon atoms, K' is alkylene of from 2 to 6, usually 2 to 4 carbon atoms, and k and k' are 1 to 6, usually 1 to 4. It is understood that the above table is merely illustrative of the more common linking groups, other linking groups being available in special situations. For example, where phenolic groups are present, such as tyrosyl, aryl diazonium functionalities may be employed. Furthermore, it is understood that the functionalities for the fluorescein and ligand or support may be reversed, with concomitant reversal of the direction of the linking group.

The subject compounds have many desirable properties. The products have significant water solubility which allow them to be conjugated to a wide variety of polypeptides, without significantly adversely affecting the water solubility of the polypeptide, nor having the polypeptide adversely affect the spectroscopic properties of the subject compounds.

As for the spectroscopic properties of the compounds, the compounds absorb at relatively long wavelengths, generally in excess of 490 nm, more usually in excess of 510 nm. Thus, naturally occurring fluorescence which may be encountered when working with physiological fluids is substantially avoided by employing exciting light at a wavelength range which does not significantly excite the naturally occurring fluorescers. In addition, the compounds have relatively sharp absorption peaks and emission peaks. Because of this, efficient overlap can be obtained between fluorescers and quenchers which allow for efficient quenching up to distances of about 70 A. The fluorescing compounds also have large Stokes shifts, so that the absorption band and emission band peaks are separated by at least 10 nm, frequently by at least 15 nm. The large Stokes shifts minimize background interference with the observed fluorescence and permit more sensitive fluorescence detection by allowing the use of optical filters with high light transmittance.

The compounds of the subject invention are prepared in accordance with conventional means. The appropriate resorcinol and carboxylic acid or anhydride are combined in the presence of a Lewis acid e.g. zinc chloride, and the mixture heated at an elevated temperature for a sufficient time to provide the desired product. The product may then be purified by conventional means.

The subject compounds find a wide variety of applications, particularly for use as conjugates to ligands and/or supports in protein binding assays. The conjugates can be used for determining qualitatively, semiquantitatively or quantitatively the presence of a compound of interest in a sample. Where the compounds are to be detected in physiological fluids, the fluids may include serum, urine, saliva, cerebral spine fluid, lymph or the like. Where the compound of interest is involved in chemical processing or ecological concerns, the sample may involve an aqueous medium, an organic medium, soil, inorganic mixtures, or the like.

For use in immunoassays or in other diagnostic situations, the spectroscopically active compounds of this invention will be conjugated to a compound of interest, including a receptor for an analyte or a ligand. (By receptor is intended any molecule which specifically binds to a spatial and polar molecular organization, while a ligand is an organic molecule having such organization.) The analyte will normally be haptenic or antigenic. Where these compounds do not have available functionalities for linking, they will be modified to introduce such a functionality, while still retaining the immunological properties in the resulting product. Those compounds which are analogs of the analyte, which analyte may also be referred to as a ligand, will be referred to as ligand analogs.

As indicated previously, the compounds of this invention may be conjugated to compounds which may be measured by known immunoassay techniques. The resulting conjugates are reagents which complete in an assay medium for the compound of interest or analyte in a sample. Therefore, the conjugate retains a sufficient proportion of the structure of the compound of interest to be able to complete with the compound of interest for receptor, usually an antibody.

The analytes or their analogs, receptors or ligands, which are conjugated to the spectroscopically active compounds of this invention are characterized by being monoepitopic or polyepitopic.

The assays will normally involve a change of spectroscopic properties due to a change in environment about the spectroscopically active compound or the bringing together of a fluorescer-quencher pair within sufficient proximity for the quencher to interact with the fluorescer. Alternatively, methods can be employed which involve the separation of associated and unassociated fluorescer and the detection of the fluorescer in one or both of the fractions.

In a first assay, steric exclusion is involved, in that receptors or antibodies for the ligand and for the fluorescer are employed, where simultaneous binding of the receptor for the ligand and receptor for the fluorescer is inhibited. Furthermore, when the receptor for the fluorescer (antifluorescer) is bound to the fluorescer, the fluorescence of the fluorescer is substantially diminished. Further reduction if not complete inhibition of fluorescence can be achieved by conjugation of quencher to the antifluorescer. This assay is extensively described in U.S. Pat. No. 3,998,943, issued Dec. 21, 1976. The fluorescein which is employed there may be substituted with the fluorescent compounds of the subject invention. The assay is described in Columns 3-5 of the subject patent, which description is incorporated herein by reference.

Generally, the method involves combining the samples suspected of containing the analyte, the conjugate of the ligand and fluorescer, anti-fluorescer, and receptor for ligand or antiligand, when ligand is the analyte. The materials are combined in an aqueous medium at a pH in the range of about 5 to 10, usually in the range of about 6 to 9, at a temperature in the range of about 10° to 45° C. and the fluorescence determined either as a rate or equilibrium mode, readings being taken within about 1 second to 1 hour after all materials have been combined for a rate mode, while for an equilibrium mode, readings may be taken for as long as up to about 24 hours or longer.

In the next immunoassay technique, a fluorescer-quencher pair is employed, where one of the members of the pair is conjugated to a member of a specific binding pair, ligand and antiligand, and the other chromophor member is bound to the same or different member of the specific binding pair. For example, the fluorescer and the quencher may be bound to different molecules of antiligand, so that when the two conjugated antiligands are brought together with antigen, the fluorescer and quencher are brought within quenching distance. Alternatively, one could bind one of the chromogens to the ligand and the other chromogen to the antiligand. This assay is extensively described in U.S. Pat. No. 3,996,345. The assay technique is described beginning with Col. 17 and ending at Col. 23, which description is incorporated herein by reference. The ratios of chromogen to ligand and receptor is described in Cols. 4–6, which description is incorporated herein by reference.

The assay is carried out in substantially the same manner as described above, except that in this assay, the fluorescer conjugates and quencher conjugates are added in conjunction with the sample and the fluorescence determined in comparison to an assay medium having a known amount of the analyte.

Other techniques may also be employed with the subject compounds, such as techniques involving heavy atom quenching as described in co-pending application Ser. No. 824,576, filed Aug. 13, 1977, now abandoned, or other assay techniques where a fluorescent molecule is desired which emits light at a wavelength substantially above the light emitted by fluorescent compounds naturally present in physiological fluids or other samples to be analyzed.

Finally, the subject conjugates may be used in conjunction with supports as described in U.S. Patent Application Ser. No. 964,099, filed November 24, 1978 now U.S. Pat. No. 4,275,149. These assays are predicated upon having the fluorescer molecule available in bulk solution for interaction with a single modulator or bound to a particle, where the particle environment prevents the interaction. Alternatively, the particle can provide an environment which modulates the fluorescent signals when the fluorescer conjugate is bound to the particle.

EXPERIMENTAL

The following examples are offered by way of illustration and not by way of limitation.

(All temperatures not otherwise indicated are centigrade. All parts and percents not otherwise indicated are by weight, except for mixtures of liquids which are by volume. The following abbreviations are employed: TLC-thin layer chromatography.

EXAMPLE I

2-Methoxy-4,5,7-trichloro-9-(2'-carboxy)-6-hydroxy-3H-xanthen-3-one

A mixture of 2,4-dihydroxy-3,5-dichloro-2'-carboxy benzophenone (160 mg, 0.05 mmole) and 2-chloro-4-methoxyresorcinol (87 mg, 0.05 mmole) was heated in an open test tube immersed in an oil bath at 190° for 10 min. The tube was cooled and the residue dissolved in 1 N sodium hydroxide (2 ml), acidified to pH 1 with conc. HCl, filtered and dried. The crude dye was dissolved in methanol and purified by TLC using acetic acid:ethyl acetate:$CH_2Cl_2$ (1:20:79). The orange fluorescent band $R_f$ 0.5 was isolated to give the product. The $\lambda_{max}^{abs}$ was 514 nm and the $\lambda_{max}^{em}$ was 541 nm in 0.05 M phosphate buffer, pH 8.0. The quantum yield was 0.8.

EXAMPLE II

2,4-dihydroxy-3,5-dichloro-2'-carboxybenzophenone

To a solution of 1 g of 2,4-dihydroxy-2'-carboxybenzophenone in 5 ml anhydrous ether, sulfuryl chloride (2 ml) was added dropwise and the solution stirred for 2 hrs. at room temperature. After removing the solvent on a Rotovap, the residue was dissolved in 10% sodium carbonate, acidified with conc. HCl and filtered. The solid was dissolved in about 1 ml ethyl acetate and added dropwise to a rapidly stirring hexane solution. The resulting precipitate was filtered and dried under vacuum to give the product (0.55 g). TLC:$R_f$ 0.6, $CH_2Cl_2$:MeOH:AcOH (89.5:10:0.5). m.p. 207° C.–210° C.

EXAMPLE III

2,4-Dihydroxy-2',4' or 5'-dicarboxybenzophenone

A mixture of the m- or p-carboxy substituted fluorescein (8 g) was added slowly to a hot (170° conc. sodium hydroxide solution (18 g sodium hydroxide in 10 ml water) and maintained at that temperature for 1.5 hr. followed by cooling and diluting with 20 ml water. After acidifying to pH 1 with conc. HCl, the resulting precipitate was filtered to give the desired product TLC $R_f$ 0.4, $CH_2Cl_2$:MeOH:AcOH (89.5:10:0.5).

EXAMPLE IV

2,4-Dihydroxy-5,3',6'-trichloro-2',4' or 5'-dicarboxybenzophenone

To a rapidly stirring solution of 3,6-dichloro-4-carboxyphthalic anhydride (5 g in 50 ml tetrachloroethane) (prepared from 3,6-dichlorobenzene-1,2,4-tricarboxylic acid by heating at 180° for 1 hr.) was added 14 g aluminum chloride and 3.4 g 4-chlororesorcinol and the mixture heated at 90° for 6 hrs. After quenching with ice and 1 N HCl, the black solution was extracted three times with ether, the combined ether extracts dried over magnesium sulfate and the ether removed in vacuo. The residue was dissolved in 5% sodium bicarbonate, the solution filtered and the basic solution extracted with ether (5×50 ml) until the extracts were clear. The aqueous layer was acidified to pH 1 with HCl and extracted with ether. The combined ether extracts were dried over magnesium sulfate and the ether evaporated to yield about 8 g of crude product. The crude product was purified by column chromatography on 200 g silica gel (Merck 60) and eluted with acetic acid:acetone:benzene (2:32:66), thereby isolating a mixture of isomers $R_f$ 0.4. The solid material was stirred with 1 N HCl overnight, filtered and dried to give 2 g of the product m.p. 203°–205° C.

Following the procedure described in Example I, except as otherwise described, the following Table III indicates a number of additional compounds which were prepared and their properties.

TABLE III

| Ex. | Product 6-hydroxy-3H—xanthen-3-one (X) | Resorcinol (R) | mg | Benzophenone B | mg |
|---|---|---|---|---|---|
| V | 2-methoxy-5,7-dichloro-2'-carboxy-X | 4-methoxy-R | 68 | 2,4-dihydroxy-3.5-dichloro-2'-carboxy-B | 164 |
| VI | 2-methyl-2',4' or 5'-dicarboxy-X | 4-methyl-R | 70 | 2,4-dihydroxy-2',4' or 5'-dicarboxy-B | 150 |
| VII | 2-methoxy-2',4' or 5'-dicarboxy-X | 4-methoxy-R | 170 | 2,4-dihydroxy-2',4' or 5'-dicarboxy-B | 300 |
| VIII | 2-methoxy-4-chloro-2',4'- or 5'-dicarboxy-X | 2-chloro-4-methoxy-R | 170 | 2,4-dihydroxy-2',4'- or 5'-dicarboxy-B | |
| IX | 2-methoxy-5,7-dichloro-2',4' or 5'-dicarboxy-X | 4-methoxy-R | | 2,4-dihydroxy-3,5-dichloro-2',4'- or 5'-dicarboxy-B[4] | |
| X | 2-methoxy-7,3',6'-trichloro-2',4'- or 5'-dicarboxy-X | 4-methoxy-R | 84 | 2,4-dihydroxy-5,3',6'-trichloro-2',4'- or 5'-dicarboxy-B | 200 |
| XI | 2-methoxy-4,5,7,3',6'-pentachloro-2',4'- or 5'-dicarboxy-X | 2-chloro-4-methoxy-R | 75 | 2,4-dihydroxy-3,5,3',6'-tetrachloro-2',4'- or 5'-dicarboxy-B[5] | 130 |
| XII | 4-methoxy-2',4'- or 5'-dicarboxy-X | 2-methoxy-R | 140 | 2,4-dihydroxy-2',4'- or 5'-dicarboxy | 300 |

| Ex. | Reaction[1] Conditions | $R_f$[2] | $\lambda_{max}$ (nm)[3] abs | em | quantum yield |
|---|---|---|---|---|---|
| V | a | 0.2 | 505 | 535 | 0.78 |
| VI | a. | 0.6 | 496 | 520 | 0.9 |
| VII | a | 0.5 | 500 | 534 | 0.78 |
| VIII | a | | 505 | 534 | 0.88 |
| IX | b. | 0.3 | 505 | 535 | 0.78 |
| X | b | 0.4 | 517 | 541 | 0.91 |
| XI | b | 0.3 | 531 | 555 | 0.82 |
| XII | c | | 501 | none | |

[1] a - Conditions of Example 1
b - Conditions of Example 1 except adding 20 mg $ZnCl_2$ with temperature of 165°
c - Conditions of Example 1 except 30 min

[2] Eluting systems are as follows:

| Ex. | Solvent | Ratio |
|---|---|---|
| 5 | AcOH:EtOAc:$CH_2Cl_2$ | 1:10:89 |
| 6 | AcOH:MeOH:$CH_2Cl_2$ | 1:15:84 |
| 7 | AcOH:$CH_2Cl_2$:EtOAc | 1:10:89 |
| 8 | AcOH:MeOH:$CH_2Cl_2$ | 1:15:85 |
| 9 | AcOH:EtOAc:$CH_2Cl_2$ | 1:20:79 |
| 10 | AcOH:Acetone:Benzene | 1:33:66 |
| 11 | AcOH:EtOAc:$CH_2Cl_2$ | 1:20:79 |
| 12 | AcOH:MeOH:$CH_2Cl_2$ | 1:15:85 |

[3] Measurement taken in 0.05 M $PO_4^{-3}$, pH 8.0
[4] Prepared from an analogous fluorescein derivative in accordance with Example 3
[5] Prepared from 2,4-dihydroxy-5,3',6'-trichloro-2',4'- or 5'-dicarboxybenzophenene in accordance with Example 2

EXAMPLE XIII

A solution of 200 mg of the product of Example XI in 3 ml dry THF containing N,N'-dicyclohexyl carbodiimide and N-hydroxy succinimide (49 mg) was stirred at room temperature overnight. Separately, t-butyl glycinate hydrochloride (1 g) was dissolved in 4 ml DMF and 1 ml triethylamine added. The resulting solution was filtered and cooled to ice-bath temperature (4°). To this was added the ester solution prepared above and the reaction mixture stirred in the cold room overnight. After removing the solvents in vacuo, the residue was stirred in hexane, filtered and dried. The crude dye was further purified by preparative TLC using AcOH-:EtOAc:CH$_2$Cl$_2$ (1:20:79), R$_f$0.7. The t-butyl ester was hydrolysed by stirring in 2 ml trifluoroacetic acid for 2 hrs. The volatiles were removed in vacuo and the residue dissolved in 10 ml 1 N sodium hydroxide, followed by acidification to pH 1 with HCl, the resulting precipitate filtered and dried in vacuo yielding 80 mg of the product. The spectroscopic properties are as follows: $\lambda_{max}^{abs}$, 531; $\lambda_{max}^{em}$, 555, quantum yield 0.82 in 0.05 M phosphate buffer, pH 8.0.

EXAMPLE XIV

A mixture of 15 mg of a product of Example XIII, 6 mg of N,N'-dicycloheyl carbodiimide and 3 mg of N-hydroxy succinimide in 1 ml THF was stirred overnight. After filtering the solution, the THF was removed in vacuo and the residue triturated with hexane. The resulting solid was filtered and washed with more hexane to yield the desired ester.

Varying ratios of the dye to protein were prepared by dissolving varying amounts of the above ester in dry DMF and adding the solution to a human IgG solution in 0.05 M phosphate buffer, pH 0.8. The reaction was allowed to proceed overnight at 0°-5° C., followed by purification over a Sephadex G-25 column prepared in 0.05 M phosphate buffer, pH 8.0. Dye to protein ratios were calculated from the UV and visible spectra by measuring absorption at 535 and 280 nm. The following indicates the ratios and a plot of the quantum yields of the various conjugates vs dye/protein ratio.

TABLE IV

| Dye/Protein mole ratio | Fluorescence Quantum Yield |
|---|---|
| 1.6 | 0.45 |
| 2.1 | 0.46 |
| 2.9 | 0.46 |
| " | 0.41 |
| 3.9 | 0.42 |
| 4.1 | 0.45 |
| 4.9 | 0.39 |
| 5.2 | 0.32 |
| 7.2 | 0.27 |
| 9.6 | 0.17 |

The subject invention provides novel compounds which have important spectroscopic properties, providing for absorption at long wavelengths, high extinction coefficients, sharp absorption bands and fluorescent bands, and substantial spacing between absorption and fluorescence bands. These properties are particularly desirable and important to the development of fluorescent techniques for the detection of a wide variety of materials. In addition, members of the subject genus can also be used as quenchers where there is a 4-oxy substituent, in having no or substantially no fluorescence emission while absorbing light at wavelengths to provide for quenching of fluorescence by a fluorescer in the excited state in close proximity to the quencher.

Although the foregoing invention has been described in some detail by way of illustration and example for purposes of clarity of understanding, it will be obvious that certain changes and modifications may be practiced within the scope of the appended claims.

What is claimed is:

1. A compound of the formula

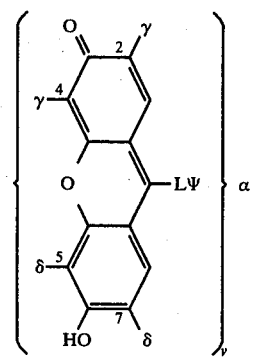

wherein:
one of the γs will be of the formula —(O)$_\epsilon\rho$ and the other is δ;
wherein $\epsilon$ is 0 or 1 and $\rho$ is an aliphatic group of from about 1 to 12 carbon atoms and 0–1 carboxyl groups;
the δ's are the same or different and are hydrogen or halogen of atomic number 17 to 80;
L is a bond or divalent organic radical of up to 20 carbon atoms;
α may be taken together with Ψ to define an active group capable of forming a stable covalent bond with carbon, nitrogen or oxygen or is an organic compound, and is at other than the ortho position when L is benzene and Ψ and α are taken together to define carboxy;
Ψ, when not taken together with α is a linking group to α;
v is 1 when Ψ is taken together with α and is otherwise on the average at least 1 and not more than the molecular weight of α divided by 500.
with the proviso that when $\epsilon$ is 0, one of the δ's may be an aliphatic group of from about 1 to 12 carbon atoms asymmetrically substituted in relation to $\rho$.

2. A compound according to claim 1 conjugated to a support.

3. A compound of the formula

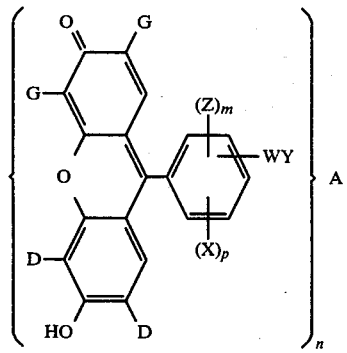

wherein:
one of the Gs is of the formula —(O)$_e$R and is otherwise D, where e is 0 or 1 and R is an aliphatic group of from 1 to 6 carbon atoms having from 0 to 1 carboxy groups;

Z is carboxy or sulphonoxy;

D is hydrogen or halogen of atom number 17 to 80;

W is a bond or divalent organic radical having up to 10 carbon atoms;

Y may be taken together with A to form an active functionality capable of forming a covalent bond with carbon, nitrogen or oxygen when not taken together with A, Y is a linking functionality;

A when not taken together with Y is a ligand or receptor of at least about 125 daltons;

X is halo of atomic number 9 to 80;

m is 1 to 3;

p is 0 to 3, with the sum of m and p being not greater than 4;

n will be 1 when Y and A are taken together or otherwise be on the average 1 to the molecular weight of A divided by 500, with the proviso that when W is a bond and Y and A are taken together to define carboxy, Y is at other than the ortho position.

4. A compound according to claim 3, wherein e is 0.

5. A compound according to claim 3, wherein e is 1.

6. A compound of the formula

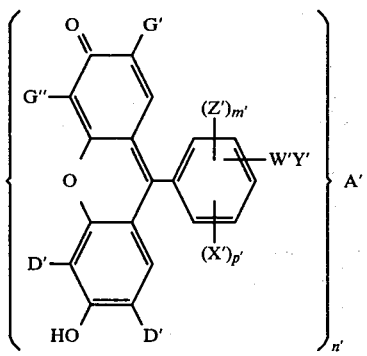

wherein:
one of G' or G" is —(O)$_{e'}$R' and is otherwise D', wherein e' is 0 or 1 and R' is alkyl of from 1 to 3 carbon atoms;

D' is hydrogen or halogen of atomic number 17 to 80;

Y' may be taken together with A' to define a non-oxo-carbonyl group and is otherwise a non-oxo-carbonyl group forming an amide group with an amino group of A';

A' when not taken together with Y', is a ligand or receptor of at least about 125 daltons;

W' is a bond or aliphatic linking group of from 1 to 12 atoms other than hydrogen, which are carbon, nitrogen, oxygen or sulfur, there being from 0 to 8 carbon atoms and 0 to 8 heteroatoms, wherein nitrogen is present as amino or amido; and oxygen and sulfur are present as oxy, oxo or the sulfur analogs thereof;

Z' is carboxy;

X' is halo of atomic number 9 to 80;

n' is 1 when Y' and A' are taken together and is otherwise on the average at least 1 to the molecular weight of A' divided by about 1,000;

m' is 0 to 2;

p' is 0 to 3, the sum of m' and p' being not greater than 4, with the proviso that, when W' is a bond and Y' and A' are taken together to define carboxy, Y' is at other than the ortho position.

7. A compound according to claim 6, wherein A' is taken together with Y'.

8. A compound according to claims 6 or 7, wherein R' is methyl.

9. A compound according to claims 6 or 7, wherein at least one of the D's and X's are chloro.

10. A compound according to claim 6, wherein A' is a ligand.

11. A compound according to claim 6, wherein A' is a receptor.

12. A compound of the formula

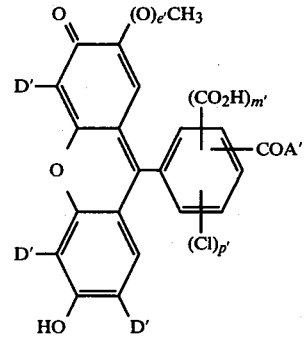

wherein:
D' is hydrogen or chloro;

e' is 0 or 1;

the sum of m' and p' is 0 to 4, wherein m' is 0 to 2;

A' is hydroxyl or a ligand or receptor of at least about 125 daltons; and

—COA' is at other than the ortho position.

13. A compound according to claim 12, wherein e' is 0.

14. A compound according to claim 12, wherein e' is 1.

15. A compound according to claims 13 and 14, wherein A' is hydroxyl.

16. A compound according to claims 13 and 14, wherein A' is a ligand.

17. A compound of the formula

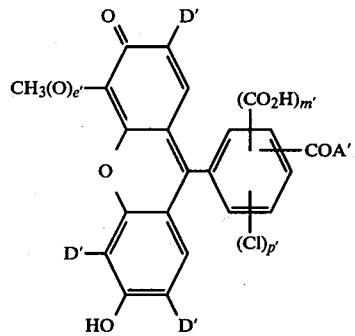

wherein:
e' is 0 or 1;

m' is 0 to 2;

p' is 0 to 3, the sum of m' and p' being not greater than 4;

D' is hydrogen or chloro; and

A' is hydroxyl or a ligand or receptor of at least about 125 daltons;

with the proviso that, when A' is hydroxyl, —COA' is at other than the ortho position.

18. A compound according to claim 17, wherein e' is 0.

19. A compound according to claim 17, wherein e' is 1.

20. A compound according to claims 17 and 18, wherein A' is hydroxyl.

21. A compound according to claims 13 or 17, bound to a support.

22. A compound according to claims 18 or 19, wherein A' is a ligand.

* * * * *